United States Patent [19]

Philion

[11] 4,396,629
[45] Aug. 2, 1983

[54] COMPOSITIONS, PROCESSES AND METHOD

[75] Inventor: Richard E. Philion, Sand Lake, N.Y.

[73] Assignee: Sterling Drug Inc., New York, N.Y.

[21] Appl. No.: 220,412

[22] Filed: Dec. 29, 1980

[51] Int. Cl.$^3$ .................. A01N 33/02; A01N 37/30
[52] U.S. Cl. ........................... 424/330; 260/501.17; 260/501.18; 260/501.19; 564/349; 424/316
[58] Field of Search ............... 564/349; 260/501.17, 260/501.18; 424/316, 330

[56] References Cited

U.S. PATENT DOCUMENTS

| | | | |
|---|---|---|---|
| 3,501,769 | 3/1970 | Crowther et al. | 564/351 X |
| 3,542,874 | 11/1970 | Keizer et al. | 260/570.7 |
| 3,712,890 | 1/1973 | Lee | 564/349 X |
| 3,732,308 | 5/1973 | Lauria et al. | 564/349 |
| 3,872,147 | 3/1975 | Koppe et al. | 564/349 X |
| 4,067,904 | 1/1978 | Comer et al. | 564/349 |
| 4,085,136 | 4/1978 | Tucker | 564/349 X |
| 4,243,681 | 1/1981 | Morrow et al. | 424/330 |
| 4,244,969 | 1/1981 | Carlsson et al. | 564/349 |

FOREIGN PATENT DOCUMENTS 2006197  5/1979  United Kingdom .

OTHER PUBLICATIONS

Burger, "Medicinal Chemistry", 3rd. Ed., Part II, pp. 1052-1055 (1970).
Kalser et al., "Journ. Med. Chem.", vol. 18, No. 7, pp. 674-683 (1975).
Hoefle et al., "Journ. Med. Chem.", vol. 18, pp. 148-152 (1975).
L. Villa et al., Il Farmaco, Ed. Sci., 24, 349-357 (1969).

Primary Examiner—Robert V. Hines
Attorney, Agent, or Firm—Paul E. Dupont; B. Woodrow Wyatt

[57] ABSTRACT

Therapeutically useful 1-(substituted-amino)-3-[4-$R_1$O-3-(lower-alkylthio, lower-alkylsulfinyl or lower-alkylsulfonyl)phenoxy]-2-propanols are obtained by reacting a 4-$R_1$O-3-(lower-alkylthio, lower-alkylsulfinyl or lower-alkylsulfonyl)phenol with an epihalohydrin and reacting the resulting product with a primary amine. The compounds have both antihypertensive and β-adrenergic blocking activity and are useful as antihypertensive agents.

31 Claims, No Drawings

COMPOSITIONS, PROCESSES AND METHOD

BACKGROUND OF THE INVENTION

1. Field of the Invention

This invention relates to compositions of matter classified in the field of chemistry as 1-(substituted amino)-3-[4-$R_1$O-3-(lower-alkylthio, lower-alkylsulfinyl or lower-alkylsulfonyl)phenoxy]-2-propanols, to processes for the preparation thereof, to pharmaceutical compositions containing the same and to the method of use thereof in reducing blood pressure in mammals.

2. Description of the Prior Art

Among various known 1-(substituted amino)-3-substituted phenoxy)-2-propanols the compounds disclosed in the following patents and publications are believed to constitute the most pertinent prior art relative to the present invention.

L. Villa et al., Il Farmaco, Ed. Sci., 24, 349–357 (1969) disclose 1-(isopropylamino)-3-[2-(methylthio)-phenoxy]-2-propanol which was prepared in connection with a study of structure-activity relationships among a group of beta-adrenolytics.

Keizer et al., U.S. Pat. No. 3,542,874, patented Nov. 4, 1970 disclose compounds of the formula:

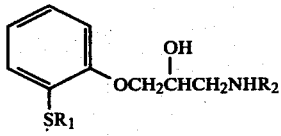

wherein:
$R_1$ is alkyl of 1 to 4 carbon atoms inclusive, and
$R_2$ is a member selected from the group consisting of alkyl of 1 to 12 carbon atoms inclusive, alkenyl of 2 to 12 carbon atoms inclusive, alkinyl of 2 to 12 carbon atoms inclusive, cycloalkyl of 3 to 12 carbon atoms inclusive and aralkyl of 7 to 12 carbon atoms inclusive. Specific compounds disclosed include those wherein $R_1$ is methyl or ethyl and $R_2$ is isopropyl; $R_1$ is methyl, ethyl or propyl and $R_2$ is tertiary butyl; $R_1$ is methyl or propyl and $R_2$ is 1-methyl-3-phenylpropyl. The compounds are stated to exhibit β-sympatholitical activity.

M. L. Hoefle, et al., J. Med. Chem., 18, 148–152 (1975) disclose in most pertinent part the compound of the following formula which is stated to have β-adrenergic blocking activity:

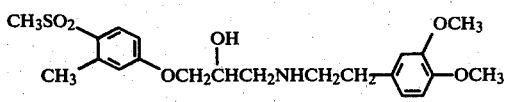

Comer et al., U.S. Pat. No. 4,067,904, patented Jan. 10, 1978 disclose a group of compounds having the formula:

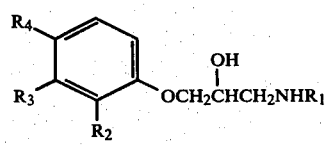

wherein
$R_1$ represents a branched-chain alkyl radical of 3 or 4 carbon atoms such as isopropyl, sec-butyl, isobutyl and t-butyl, phenoxyisopropyl, 4-hydroxy-α,α-dimethylphenethyl, 4-methoxy-α,α-dimethylphenethyl or cycloalkyl of 3 to 6 carbon atoms inclusive;
$R_2$ represents hydrogen, lower-alkyl or lower-alkylsulfonyl;
$R_3$ represents hydrogen or lower-alkyl and
$R_4$ represents hydrogen or lower-alkylsulfonyl, only one of $R_2$ and $R_4$ being lower-alkylsulfonyl. Specific compounds disclosed include those wherein $R_1$ is isopropyl or t-butyl, $R_2$ is hydrogen, $R_3$ is hydrogen or methyl and $R_4$ is methylsulfonyl; $R_1$ is isopropyl, $R_2$ is methylsulfonyl, $R_3$ and $R_4$ are each hydrogen; $R_1$ is 4-methoxy(or 4-hydroxy)-α,α-dimethylphenethyl, $R_2$ is hydrogen, $R_3$ is methyl and $R_4$ is methylsulfonyl. The compounds are stated to possess anti-arrhythmic and/or cardioselective β-adrenergic blocking properties and to be useful in the treatment of hypertension.

Belgian Pat. No. 871,143, published Apr. 10, 1979 and equivalent United Kingdom Patent Application No. 2,006,197A, published May 2, 1979, disclose a group of compounds having the formula

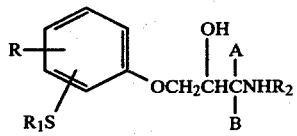

wherein
A, B and R are hydrogen or 1–4C alkyl;
$R_1$ is 1–8C alkyl and
$R_2$ is 6–12C alkyl or (5–8C)cycloalkyl-(2–6C)alkyl including the species wherein A, B and R are hydrogen, $R_2$ is octyl and $R_1$S is 3-isopropylthio. The compounds are stated to increase peripheral blood flow, relax vascular smooth muscle and inhibit thromboctye aggregation, but to be practically free of β-adrenergic blocking activity.

SUMMARY OF THE INVENTION

The present invention provides novel, therapeutically useful compounds which have both anti-hypertensive and β-adrenergic blocking activity and which are indicated for use as antihypertensive agents.

In a composition of matter aspect the invention relates to 1-(substituted amino)-3-[4-$R_1$O-3-(lower-alkylthio, lower-alkylsulfinyl or lower-alkylsulfonyl)-phenoxy]-2-propanols which are useful as antihypertensive agents.

In a further composition of matter aspect the present invention provides a pharmaceutical composition comprising a 1-(substituted amino)-3-[4-$R_1$O-3-(lower-alkylthio, lower-alkylsulfinyl or lower-alkylsulfonyl)-phenoxy]-2-propanol in admixture with a pharmaceutically acceptable excipient.

In one of its process aspects this invention relates to a process for preparing 1-(substituted amino)-3-[4-$R_1$O-3-(lower-alkylthio, lower-alkylsulfinyl or lower-alkylsulfonyl)phenoxy]-2-propanols which comprises reacting 4-$R_1$O-3-(lower-alkylthio, lower-alkylsulfinyl or lower-alkylsulfonyl)phenol with an epihalohydrin followed by reaction of the product obtained thereby with a substituted amine.

In another process aspect the invention provides a process for preparing 1-(substituted amino)-3-[4-$R_1$O-3-(lower-alkylthio)phenoxy]-2-propanols which comprises reducing the corresponding 1-(substituted amino)-3-[4-$R_1$O-3-(lower-alkylsulfinyl)phenoxy]-2-propanols.

In yet another process aspect the present invention relates to a process for preparing 1-(substituted amino)-3-[4-hydroxy-3-(lower-alkylthio, lower-alkylsulfinyl or lower-alkylsulfonyl)phenoxy]-2-propanols which comprises debenzylating the corresponding 1-(substituted amino)-3-[4-benzyloxy-3-(lower-alkylthio, lower-alkylsulfinyl or lower-alkylsulfonyl)phenoxy]-2-propanols.

In its method aspect the present invention provides a method of reducing blood pressure in a mammal in need of such treatment which comprises administering to said mammal in an amount effective in lowering blood pressure a 1-(substituted amino)-3-[4-$R_1$O-3-(lower-alkylthio, lower-alkylsulfinyl or lower-alkylsulfonyl)-phenoxy]-2-propanol of this invention.

DETAILED DESCRIPTION OF THE INVENTION INCLUSIVE OF THE PREFERRED EMBODIMENTS

More specifically, the invention sought to be patented resides, in a composition of matter aspect, in 1-(substituted amino)-3-[4-$R_1$O-3-(lower-alkylthio, lower-alkylsulfinyl or lower-alkylsulfonyl)phenoxy]-2-propanols useful as antihypertensive agents having Formula I hereinbelow:

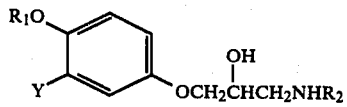

wherein:
Y is lower-alkylthio, lower-alkylsulfinyl or lower-alkylsulfonyl;
$R_1$ is hydrogen, lower-alkyl or benzyl;
$R_2$ is lower-alkyl or

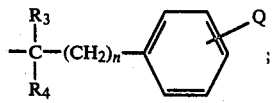

in which:
$R_3$ and $R_4$ are independently hydrogen or lower-alky;
Q is hydrogen, lower-alkyl, hydroxy or lower-alkoxy;
n is 1, 2 or 3; and
acid-addition salts thereof.

In a further composition aspect the invention sought to be patented resides in a pharmaceutical composition comprising a compound of Formula I hereinabove in admixture with a pharmaceutically acceptable excipient.

In one of its process aspects the invention sought to be patented resides in a process for producing the 1-(substituted amino)-3-[4-$R_1$O-3-(lower-alkylthio, lower-alkylsulfinyl or lower-alkylsulfonyl)phenoxy]-2-propanols of Formula I hereinabove which comprises reacting a 4-$R_1$O-3-(lower-alkylthio, lower-alkylsulfinyl or lower-alkylsulfonyl)phenol having Formula II hereinbelow

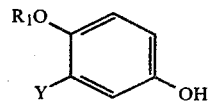

with an eiphalohydrin having Formula III hereinbelow

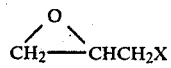

in the presence of a base, and reacting the resulting product with an amine having Formula IV hereinbelow $R_2NH_2$           IV where in above Formulas II, III and IV the substituents Y, $R_1$ and $R_2$ have the previously given meanings and X is chloro, bromo or iodo.

In a further process aspect the invention sought to be patented resides in the process for preparing the 1-(substituted amino)-3-[4-($R_1$O-3-(lower-alkylthio)phenoxy]-2-propanols of Formula I hereinabove wherein $R_2$ has the previously given meaning, $R_1$ is lower-alkyl or benzyl and Y is lower-alkylthio, which comprises reducing the corresponding 1-(substituted amino)-3-[4-$R_1$O-3-(lower-alkylsulfinyl)phenoxy]-2-propanols of Formula I wherein $R_2$ has the above-given meaning, $R_1$ is lower-alkyl or benzyl and Y is lower-alkylsulfinyl.

In another process aspect, the invention provides a process for preparing 1-(substituted amino)-3-[4-hydroxy-3-(lower-alkylthio, lower-alkylsulfinyl or lower-alkylsulfonyl)phenoxy]-2-propanols of Formula I hereinabove (Y and $R_2$ have the previously given meanings and $R_1$ is hydrogen) which comprises debenzylating the corresponding 1-(substituted amino)-3-[4-benzyloxy-3-(lower-alkylthio, lower-alkylsulfinyl or lower-alkylsulfonyl)phenoxy]-2-propanols of Formula I (Y and $R_2$ have the previously given meanings and $R_1$ is benzyl).

In its method aspect the invention sought to be patented resides in the method of reducing blood pressure in a mammal which comprises administering to said mammal in an amount effective in lowering blood pressure a 1-(substituted amino)-3-[4-$R_1$O-3-(lower-alkylthio, lower-alkylsulfinyl or lower-alkylsulfonyl)-phenoxy]-2-propanol of Formula I hereinabove.

In the terms of lower-alkyl, lower-alkoxy, lower-alkylthio, lower-alkylsulfinyl and lower-alkylsulfonyl, "lower" denotes an alkyl moiety having from 1 to 4 carbon atoms which can be arranged as a straight or branched chain. There are included methyl, ethyl, n-propyl, isopropyl, n-butyl, sec-butyl, isobutyl and t-butyl.

Due to the presence of the basic amino grouping, the free base forms of the products represented by Formula I react with organic and inorganic acids to form acid addition salts.

The compounds of the invention are useful both in the free base form and in the form of acid-addition salts, and both forms are within the purview of the invention. The acid-addition salts are simply a more convenient form for use, and in practice, use of the salt form inherently amounts to use of the base form.

The acid-addition salts are prepared from any organic or inorganic acid. They are obtained in conventional fashion, for instance either by direct mixing of the base with the acid, or, when this is not appropriate, by dissolving either or both the base and the acid separately in water or an organic solvent and mixing the two solutions, or by dissolving both the base and the acid togehter in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, dibenzoyl-tartaric acid, oxalic acid, pyromucic acid, citric acid, lactic acid, mandelic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacedic acid, barbituric acid, cyclohexylsulfamic acid, isethionic acid, methanesulfonic acid, benzenesulfonic acid, p-toluenesulfonic acid, 1,4-naphthalenedisulfonic acid, butylarsonic acid, methanephosphonic acid, acidic resins, hydrofluoric acid, hydrochloric acid hydrobromic acid, hydriodic acid, perchloric acid, nitric acid, sulfuric acid, sulfamic acid, glutaric acid, phosphoric acid, arsenic acid and the like.

All the acid-addition salts are useful as sources of the free base form, by reaction with an inorganic base. It will thus be appreciated that if one or more of the characteristics such as solubility, crystallinity, molecular weight, physical appearance, toxicity, or the like of a given base or acid-addition salt thereof render that form unsuitable for the purpose at hand it can be readily converted, in accordance with procedures well known in the art, to another more suitable form.

When the compounds of the invention are to be utilized for pharmaceutical purposes, the acids used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Appropriate medicinally acceptable salts within the scope of the invention are those derived from acids such as hydrochloric acid, acetic acid, lactic acid, tartaric acid, cyclohexylsulfamic acid, methanesulfonic acid, phosphoric acid and the like.

The compounds of the invention represented by Formula I wherein $R_1$ is hydrogen are, of course, amphoteric, having both acidic phenol and basic amino groups and thus, form salts with both acids and bases.

Compounds of Formula I contain at least one and as many as three asymmetric centers, i.e. the carbinol carbon atom, the sulfur atom when Y is lower-alkylsulfinyl and the carbon to which $R_3$ and $R_4$, when dissimilar, are attached, when $R_2$ is

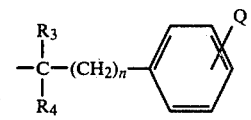

Hence, said compounds can exist in as many as eight stereochemically isomeric forms all of which, either individually or as mixtures of any two or more, are considered within the purview of this invention. If desired, the isolation or the production of a particular stereochemical form or of a mixture of two or more stereochemical forms can be accomplished by application of general principles known in the art. Thus, enantiomers can be separated by conventional methods of resolution employing known resolving agents such as d-tartaric acid, dibenzoyl-d-tartaric acid or d-mandelic acid, and diastereomers can be separated by fractional crystallization or by conventional chromatographic techniques.

The manner and process for making and using the invention and the best mode contemplated by the inventor of carrying it out will now be described so as to enable any person skilled in the art to which it pertains to make and use the same.

The compounds of Formula I are obtained in accordance with the present invention by reacting a phenol of Formula II with excess epihalohydrin of Formula III in a basic medium such as aqueous alkali metal hydroxide or carbonate and reacting the resulting product with excess amine of Formula IV.

The first step of the process is conveniently carried out by reacting the phenol (Formula II) with excess epihalohydrin (Formula III), e.g. epichlorohydrin, in aqueous base, e.g. sodium or potassium hydroxide, optionally in a co-solvent such as tetrahydrofuran or dioxane at about ambient temperature until the reaction is essentially complete as indicated by thin layer chromatography. Sufficient base is used in the reaction to maintain an alkaline medium. Thus, when the phenol of Formula II contains one acidic proton, i.e. when $R_1$ is lower-alkyl or benzyl, approximately one equivalent of base is used. However, when two acidic protons are present, i.e. when $R_1$ in Formula II is hydrogen, about two equivalents of base are employed.

It will be appreciated that the epihalohydrin of Formula III can undergo substitution at either the halogen-bearing carbon or the epoxide ring. Accordingly, reaction with a phenol of Formula II can and ordinarily does produce a mixture of a halohydrin of Formula V and an epoxide of Formula VI hereinbelow.

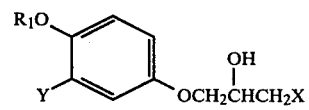

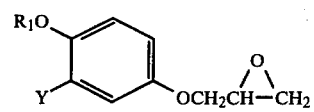

Although if desired, this mixture can be separated by conventional means, such separation is neither necessary nor advantageous since each of the compounds of Formulas V and VI yeilds the same product of Formula I on reaction with an amine of Formula IV. It is therefore ordinarily preferred to simply react the mixture of halohydrin and epoxide directly with the amine.

Reaction of a 2-(lower-alkylsulfinyl or lower-alkylsulfonyl)-1,4-hydroquinone (Formula II wherein $R_1$ is hydrogen and Y is lower-alkylsulfinyl or lower-alkylsulfonyl) with an epihalohydrin in the presence of two molar equivalents of base occurs selectively at the 4-hydroxyl group to ultimately afford the desired final product of Formula I. Presumably, reaction proceeds through the dianion of the 1,4-hydroquinone which undergoes alkylation at the more basic 4-hydroxy anion. On the other hand, reaction of the corresponding 2-(lower-alkylthio)-1,4-hydroquinone (Formula II wherein $R_1$ is hydrogen and Y is lower-alkylthio) with epihalohydrin is non-selective and can take place at either hydroxyl group to give a mixture. Hence, in preparing a compound of Formula I wherein $R_1$ is hydrogen and Y is lower-alkylthio it is ordinarily preferred to employ as starting material a phenol of Formula II wherein $R_1$ is a removable protecting group such as benzyl in order to insure that reaction with epihalohydrin will occur at the 4-hydroxyl group. The benzyl group can then be removed at a subsequent stage in the process as described hereinbelow.

The second step of the process is conveniently carried out by heating the reaction product of a phenol of Formula II and an epihalohydrin of Formula III with a large excess of an amine of Formula IV, optionally in a suitable solvent such as ethanol, 2-propanol, acetonitrile or N,N-dimethylformamide, at about 25°–150° C. preferably 75°–100° C. until the reaction is essentially complete as indicated by thin layer chromatography. The product is isolated and purified as either the free base or an acid-addition salt thereof employing conventional methods.

In addition to the above-described procedures, the compounds of Formula I wherein Y is lower-alkylthio can also be obtained by reducing the corresponding compounds of Formula I wherein Y is lower-alkylsulfinyl with an appropriate reducing agent in a suitable solvent such as sodium borohydride/cobalt chloride in water or a lower-alkanol, e.g. ethanol. It has been found, however, that a free hydroxyl group adjacent the lower-alkylsulfinyl group interferes with reduction of the latter. Accordingly, when carrying out this reduction it is preferred that $R_1$ be lower-alkyl or benzyl, the latter group, of course, being removable in a subsequent step if desired.

It will be appreciated that the compounds of Formula I hereinabove wherein $R_1$ is benzyl can be debenzylated to give the corresponding hydroxy compounds of Formula I wherein $R_1$ is hydrogen. Debenzylation can be achieved either by hydrogenolysis in the presence of a noble metal catalyst, e.g. palladium, in a suitable solvent such as acetic acid, or by acidic cleavage which is conveniently carried out by heating the benzyloxy compound in trifluoroacetic acid under reflux for about 1 to 2 hours. Although the lower-alkylsulfinyl and lower-alkylsulfonyl-substituted benzyloxy compounds (Formula I wherein $R_1$ is benzyl and Y is lower-alkylsulfinyl or lower-alkylsulfonyl) can be debenzylated by catalytic hydrogenolysis, in view of the known inhibitory effect of sulfides on noble metal catalysts it is preferred to debenzylate the corresponding lower-alkylthio compounds (Formula I wherein $R_1$ is benzyl and Y is lower-alkylthio) through acidic cleavage with trifluoroacetic acid.

The intermediate phenols of Formula II hereinabove are prepared from the generally known 2-(lower-alkylthio)-1,4-hydroquinones, i.e. the compounds of Formula II wherein $R_1$ is hydrogen and Y is lower-alkylthio described by Ukai and Hirose, Chem. Pharm. Bull., 16, 195–201 (1968). Thus, the 2-(lower-alkylsulfinyl or lower-alkylsulfonyl)-1,4-hydroquinones (Formula II wherein $R_1$ is hydrogen and Y is lower-alkylsulfinyl or lower-alkylsulfonyl) are obtained by oxidizing the corresponding lower-alkylthio compounds with an appropriate oxidizing agent such as a peracid, hydrogen peroxide or sodium metaperiodate. The oxidation is preferably carried out by treating the 2-(lower-alkylthio)-1,4 hydroquinone with commercial 50% peracetic acid in methanol for approximately 0.25 to 2.5 hours, or until oxidation is substantially complete as indicated by thin layer chromatography. Use of one molar equivalent of peracetic acid at −10° to 10° C. affords the lower-alkylsulfinyl compound whereas the use of two molar equivalents of peracetic acid at 10°–30° C. produces the corresponding lower-alkylsulfonyl compound.

The intermediate phenols of Formula II wherein $R_1$ is lower-alkyl or benzyl and Y is RS, RSO— or $RSO_2$—, R being lower-alkyl, are obtained in accordance with the following reaction scheme:

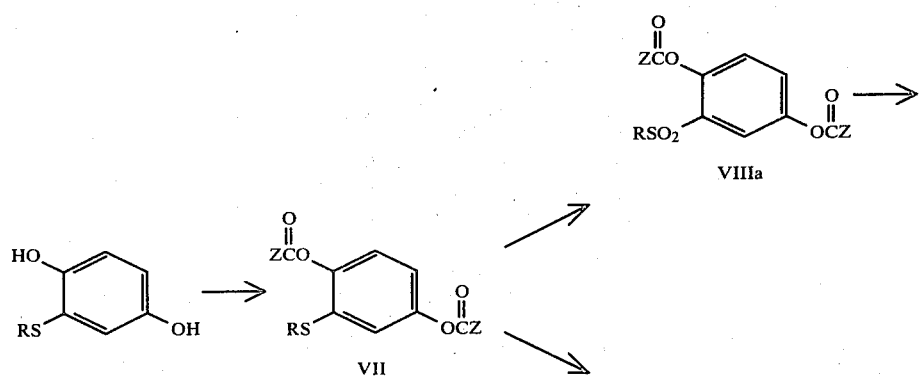

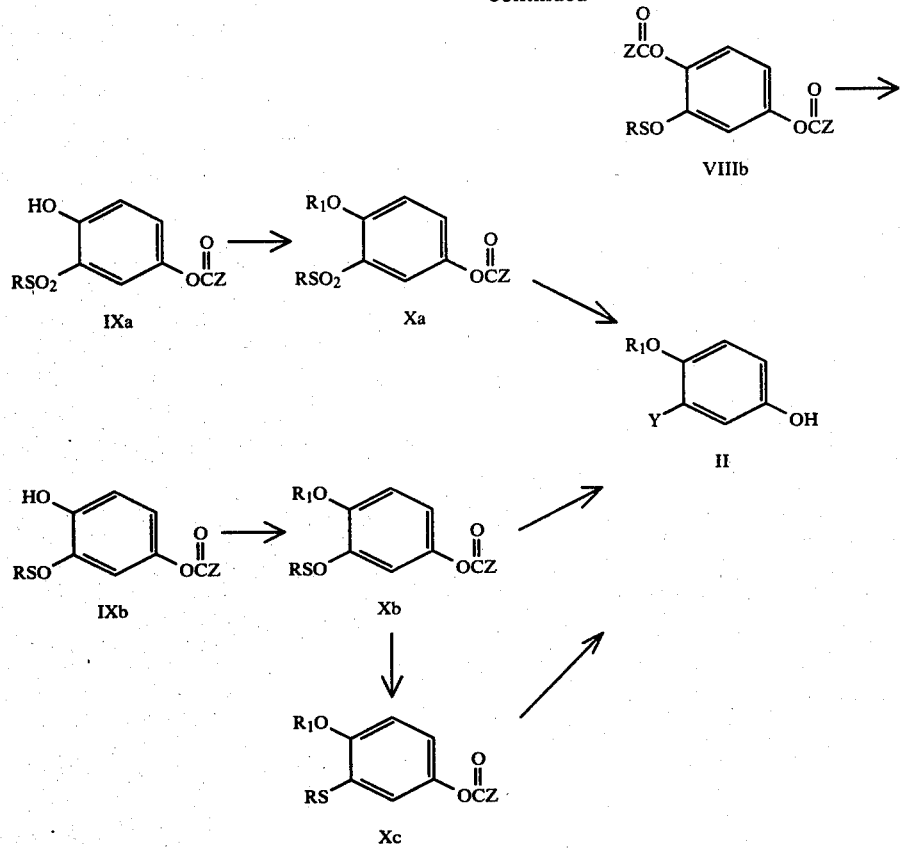

Thus, a 2-RS-1,4-hydroquinone is esterified by reaction with an acyl halide or anhydride, for example benzoyl chloride or acetic anhydride, optionally in the presence of an acid acceptor such as a tertiary amine or pyridine to give the diester having Formula VII ($Z = C_6H_5$ or $CH_3$). The diester is then oxidized in accordance with the previously described oxidation procedure to afford the corresponding sulfone and sulfoxide of Formulas VIIIa and VIIIb, respectively. The latter compounds are then selectively hydrolyzed by reaction with one molar equivalent of sodium bicarbonate in aqueous methanol at about 50°–60° C. The resulting monohydroxy compounds of Formulas IXa and IXb are alkylated in accordance with conventional procedures, for example by reaction with a lower-alkyl or benzyl halide or tosylate, e.g. methyl iodide or benzyl chloride in an appropriate solvent such as acetone, tetrahydrofuran or N,N-dimethylfomamide in the presence of an acid acceptor such as sodium or potassium carbonate to give the $R_1O$ compounds of Formula Xa and Xb. If desired, the lower-alkylsulfinyl compound of Formula Xb is reduced to the corresponding lower-alkylthio compound of Formula Xc in accordance with the procedure described hereinabove for reducing the 3-(lower-alkylsulfinyl) compounds of Formula I to the corresponding 3-(lower-alkylthio) compounds. The monoesters of Formulas Xa, Xb and Xc are then hydrolyzed with aqueous sodium or potassium hydroxide, optionally in the presence of a co-solvent such as ethanol or tetrahydrofuran, to give the phenols of Formula II wherein $R_1$ is lower-alkyl or benzyl and Y is lower-alkylthio, lower-alkylsulfinyl or lower-alkylsulfonyl.

In carrying out the method aspect of this invention, i.e. the method of lowering blood pressure in a mammal in need of such treatment, which comprises administering to said mammal in an amount effective in lowering blood pressure a compound having Formula I hereinabove, said compounds can be administered orally in the form of pills, tablets, capsules, e.g. in admixture with talc, starch, milk sugar or other inert, i.e. non-toxic or pharmacologically acceptable pharmaceutical carrier, or in the form of aqueous solutions, suspensions, encapsulated suspensions, gels, elixirs, aqueous alcoholic solutions, e.g. in admixture with sugar or other sweetening agents, flavorings, colorings, thickeners and other conventional pharmaceutical excipients. When injected subcutaneously, intramuscularly or intravenously, they can be administered, e.g. as an aqueous or peanut oil solution or suspension using excipients and carriers conventional for this mode of administration. The best route of administration and the best dosage will be apparent from the laboratory tests for activity and toxicity of the selected compound conventionally undertaken as part of the development phase of a pharmaceutical. Ordinarily, an oral dosage unit contains about 1 to 50 mg. of the active medicament and is administered as often as required to maintain a desired blood pressure reduction, for example one to three times daily.

The molecular structures of the compounds of the invention were assigned on the basis of the method of their preparation and study of their infrared and nuclear magnetic resonance spectra, and confirmed by the correspondence between calculated and found values for the elemental analyses of representative examples.

The invention is illustrated by the following examples without, however, being limited thereto.

EXAMPLE 1

A. Dry hydrogen chloride was bubbled into a solution containing 110 g. of 1,4-hydroquinone in 80 ml. of dimethylsulfoxide and 100 ml. of methanol until the solution was saturated. After stirring three hours, the methanol was evaporated and the residue was diluted with acetonitrile. The resulting crystalline product was collected by filtration and washed with acetonitrile and ether to give 137 g. of (2,5-dihydroxyphenyl)dimethylsulfonium chloride. The mother liquors afforded a second crop of 21 g.

B. A mixture containing 150 g. of (2,5-dihydroxyphenyl)dimethylsulfonium chloride in 210 ml. of benzoyl chloride was stirred and heated to a temperature of 145° C. Heating was discontinued and the mixture stirred until the temperature dropped to 80° C. The reaction mixture was diluted with 300 ml. of methanol and cooled in an ice bath. The resulting crystalline product was collected by filtration and washed with cold methanol and hexane to give 247 g. of 2-(methylthio)-1,4-hydroquinone dibenzoate.

C. To a solution containing 247 g. of 2-(methylthio)-1,4-hydroquinone dibenzoate in 1.5 liter of acetone and 300 ml. of methanol was added dropwise over 30 minutes, 114 ml. of 50% peracetic acid. After the addition was complete, the reaction mixture was diluted with 400 ml. of water and set aside in a freezer for two days. The resulting white crystalline product was collected by filtration and dried to give 248 g. of 2-(methylsulfinyl)-1,4-hydroquinone dibenzoate, m.p. 121°–122° C.

D. To a stirred solution containing 240 g. of 2-(methylsulfinyl)-1,4-hydroquinone dibenzoate in 1.8 liters of methanol at 50°–60° C. was added dropwise a solution containing 50 g. of sodium bicarbonate in 300 ml. of warm water. After stirring two hours at 50°–60° C., one-half hour at about 40° C. and one-half hour at about 50° C., the pH was adjusted to about 7.5 with acetic acid and the reaction mixture was concentrated until the product began to crystallize. Crystallization was then allowed to continue in the freezer overnight. The resulting 140 g. of white crystalline solid was combined with another 20 g. of product obtained from the filtrate, slurried in 300 ml. of ether and filtered to give 153 g. of 4-benzoyloxy-2-(methylsulfinyl)phenol, m.p. 162°–165° C.

E. A mixture containing 100 g. of 4-benzoyloxy-2-(methylsulfinyl)phenol in 1 liter of N,N-dimethylformamide, 200 ml. of methyl iodide and 48 g. of milled potassium carbonate was stirred 2.75 hours at room temperature. The reaction mixture was treated with 20 ml. of acetic acid and then diluted with water and extracted successively with ether and methylene dichloride. The organic extracts were washed with water followed by saturated aqueous sodium chloride, dried over anhydrous sodium sulfate and evaporated to dryness. The product which began to crystallize was slurried with a mixture of isopropyl acetate and hexane, and collected by filtration to give 83 g. of 4-methoxy-3-(methylsulfinyl)phenyl benzoate, m.p. 115° C.

F. A solution containing 83 g. of 4-methoxy-3-(methylsulfinyl)phenyl benzoate in 1 liter of tetrahydrofuran was combined with a solution containing 16 g. of potassium hydroxide in 40 ml. of water and 160 ml. of ethanol. The resulting mixture was stirred under nitrogen at room temperature for 4.5 hours. The mixture was neutralized with acetic acid, diluted with water and extracted with chloroform. The chloroform extracts were washed successively with water and saturated aqueous sodium chloride, and evaporated to dryness. The product which began to crystallize was slurried in hexane, collected by filtration and dried to give 47 g. of 4-methoxy-3-(methylsulfinyl)phenol, m.p. 173°–174° C.

G. To a stirred suspension of 24.6 g. of 4-methoxy-3-(methylsulfinyl)phenol in 250 ml. of water was added a solution containing 5.3 g. of sodium hydroxide in 30 ml. of water. To the resulting clear solution was added 150 ml. of epichlorohydrin and 100 ml. of tetrahydrofuran. After stirring the biphasic mixture three hours, the layers were separated and the aqueous layer was extracted with methylene dichloride. The combined organic fractions were dried over anhydrous sodium sulfate and evaporated to dryness leaving 35 g. of colorless oil indicated by nmr spectroscopy to comprise a mixture of 3-[4-methoxy-3-(methylsulfinyl)phenoxy]-1-chloro-2-propanol and 3-[4-methoxy-3-(methylsulfinyl)phenoxy]-1,2-epoxypropane. A mixture containing this material, 150 ml. of 2-propanol and 100 ml. of t-butylamine was heated under reflux overnight and then evaporated to dryness. The residue was dissolved in methylene dichloride and the resulting solution was washed successively with aqueous sodium bicarbonate and saturated aqueous sodium chloride, dried over anhydrous sulfate and evaporated to dryness to give 22 g. of 1-(t-butylamino)-3-[4-methoxy-3-(methylsulfinyl)phenoxy]-2-propanol [Formula I: $Y=CH_3SO$, $R_1=CH_3$, $R_2=C(CH_3)_3$] as a colorless oil.

Another similar preparation employing 10.0 g. of 4-methoxy-3-(methylsulfinyl)phenol, 1.4 g. of sodium hydroxide, 100 ml. of epichlorohydrin and 150 ml. of t-butylamine and converting the resulting product to the hydrochloride in conventional manner afforded 10.1 g. of the corresponding hydrochloride, m.p. 198°–200° C.

H. A mixture containing 20 g. of 1-(t-butylamino)-3-[4-methoxy-3-(methylsulfinyl)phenoxy]-2-propanol and 31 g. of colbalt chloride hexahydrate in 500 ml. of 95% ethanol was cooled in an ice bath and treated portionwise with 25 g. of sodium borohydride. After stirring overnight, the reaction mixture was diluted with water, heated 0.5 hour on a steam bath and then concentrated under vacuum. The residue was extracted with ethyl acetate and the resulting extract was evaporated to dryness. The residue was dissolved in ether, washed thoroughly with water followed by saturated aqueous sodium chloride and evaporated to dryness to give 12.5 g. of a colorless oil which crystallized on standing. This material was converted to the hydrochloride salt and recrystallized twice from 2-propanol to give, after drying, 7.6 g. of 1-(t-butylamino)-3-[4-methoxy-3-(methylthio)phenoxy]-2-propanol hydrochloride [Formula I: $Y=CH_3S$, $R_1=CH_3$, $R_2=C(CH_3)_3$], m.p. 169°–171° C.

EXAMPLE 2

Following a procedure similar to that described in Example 1G, but employing 10.0 g. of 4-methoxy-3-(methylsulfinyl)phenol, 2.4 g. of sodium hydroxide and 100 ml. of epichlorohydrin there was obtained 14 g. of a colorless oil which was heated 0.5 hour on a steam bath with 80 ml. of d(+)-1-methyl-3-(4-methoxyphenyl)propylamine and then stirred overnight at room temperature. Most of the unreacted amine was removed by distillation under water aspirator vacuum at 130° C. The residual oil was washed thoroughly with water, diluted with 200 ml. of methylene dichloride, and the resulting solution washed thoroughly with 1.5 N hydrochloric acid followed by saturated aqueous sodium chloride, dried over anhydrous sodium sulfate and evaporated to dryness. The resulting gum was crystallized from ether and acetone and then from acetone and ethyl acetate to give 14.5 g. of a tan solid. Recrystallization of 8.6 g. of this material from acetonitrile afforded, after drying, 6.5 g. of 1-[4-methoxy-3-(methylsulfinyl)phenoxy]-3-[[3-(4-methoxyphenyl)-1-methylpropyl]amino]-2-propanol hydrochloride [Formula I: $Y=CH_3SO$, $R_1=CH_3$,

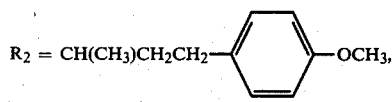

m.p. 147°–149° C. $[\alpha]_D^{25}=+6.6°$ C. (2% in methanol).

EXAMPLE 3

A mixture containing 75 g. of 4-benzoyloxy-2-(methylsulfinyl)phenol, 37 g. of benzylchloride and 37 g. of milled potassium carbonate in 500 ml. of N,N-dimethylformamide was stirred overnight at room temperature and then heated 0.75 hour on a steam bath. The reaction mixture was filtered and the filtrate diluted with ethyl acetate and washed with water followed by saturated aqueous chloride. After drying over anhydrous sodium sulfate the ethyl acetate solution was evaporated to dryness and the residue diluted with ether. The resulting crystalline product was collected by filtration to give 87 g. of 4-benzyloxy-3-(methylsulfinyl)phenyl benzoate.

B. A solution containing 45 g. of 4-benzyloxy-3-(methylsulfinyl)phenyl benzoate in 500 ml. of ethanol was combined with a solution of 5.6 g. of sodium hydroxide in 50 ml. of water and the resulting mixture was heated one hour on the steam bath and then evaporated to dryness. The residue was dissolved in chloroform and the resulting solution washed successively with water and saturated aqueous sodium chloride. The chloroform solution was dried over anhydrous sodium sulfate and evaporated to dryness. Crystallization of the residue from hexane-ether afforded, after drying, 31 g. of 4-benzyloxy-3-(methylsulfinyl)phenol.

C. A mixture containing 30 g. of 4-benzyloxy-3-(methylsulfinyl)phenol, 150 ml. of epichlorohydrin, 300 ml. of water, 200 ml. of tetrahydrofuran and a solution containing 4.4 g. of sodium hydroxide in 40 ml. of water was stirred at room temperature for two days. The layers were separated and the organic portion was diluted with methylene dichloride and then washed with water followed by saturated aqueous sodium chloride. The methylene dichloride solution was dried over anhydrous sodium sulfate and evaporated to dryness to give 42 g. of oil indicated by nmr spectroscopy to comprise a mixture of 3-[4-benzyloxy-3-(methylsulfinyl)phenoxy]-1-chloro-2-propanol and 3-[4-benzyloxy-3-(methylsulfinyl)phenoxy]-1,2-epoxypropane. The material was combined with 85 ml. of d(+)-1-methyl-3-(4-methoxyphenyl)propylamine and heated overnight at 90° C. Unreacted amine was removed by distillation under vacuum (100° C. at 0.1 mm. Hg.), and the residue was dissolved in methylene dichloride. The resulting solution was washed successively with dilute hydrochloric acid, water and saturated aqueous sodium chloride, dried over anhydrous sodium sulfate and evaporated to dryness. The residue was dissolved in a mixture of ether and isopropyl acetate, and the resulting solution washed with aqueous ammonia, then filtered through a 2.5-inch column of alumina to remove a non-polar impurity after which the desired product was eluted from the alumina with ether, followed by ethyl acetate to give 28 g. of 1-[4-benzyloxy-3-(methylsulfinyl)phenoxy]-3-[[3-(4-methoxyphenyl)-1-methylpropyl]amino]-2-propanol [Formula I: $Y=CH_3SO$, $R_1=C_6H_5CH_2$,

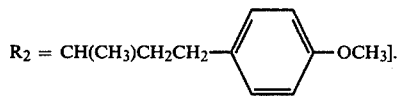

D. A solution containing 15.5 g. of 1-[4-benzyloxy-3-(methylsulfinyl)phenoxy]-3-[[3-(4-methoxyphenyl)-1-methylpropyl]amino]-2-propanol in 160 ml. of trifluoroacetic acid was heated 1.75 hours under reflux and then evaporated to dryness under vacuum. The residue was dissolved in chloroform and the resulting solution was washed with aqueous sodium bicarbonate followed by saturated aqueous sodium chloride. The chloroform solution was then dried over anhydrous sodium sulfate, filtered, diluted with acetone and acidified with ethereal hydrogen chloride. After standing two days at room temperature, 3.8 g. of product, which had crystallized, was collected by filtration and combined with 5.6 g. of product obtained in another similar preparation. The combined material was recrystallized from methanol-acetone to give 7.3 g. of 1-[4-hydroxy-3-(methylsulfinyl)phenoxy]-3-[[3-(4-methoxyphenyl)-1-methylpropyl]amino]-2-propanol hydrochloride [Formula I: $Y=CH_3SO$, $R_1=H$,

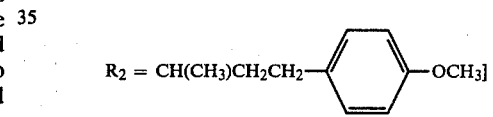

m.p. 190°–195° C. $[\alpha]_D^{25}=+14.4°$ (2% in methanol).

EXAMPLE 4

A. A mixture containing 60 g. of (2,5-dihydroxyphenyl)dimethylsulfonium chloride and 250 ml. of N,N-diemthylformamide was heated on the steam bath until the evolution of methyl chloride had ceased (approximately 0.5 hour). The reaction mixture was evaporated nearly to dryness under vacuum and then subjected to azeotropic distillation with xylene. The residue was then dissolved in a mixture of ether and isopropyl acetate and the resulting solution washed with dilute aqueous sodium chloride followed by saturated aqueous sodium chloride. Evaporation of the organic salts afforded an oil which readily crystallized. This material was slurried in methylene dichloride and stored overnight in a freezer. The crystalline product was collected by filtration, washed with hexane and dried to give 31 g. of 2-(methylthio)-1,4-hydroquinone.

B. To a solution containing 15.6 g. of 2-(methylthio)-1,4-hydroquinone in 120 ml. of methanol, cooled in an ice-acetone bath was added dropwise over 0.5 hour 15 ml. of 40% peracetic acid. The reaction mixture was evaporated to dryness under vacuum and the residue triturated with methylene dichloride to give 16.3 g. of 2-(methylsulfinyl)-1,4-hydroquinone.

C. A mixture containing 16 g. of 2-(methylsulfinyl)-1,4-hydroquinone, 7.45 g. of sodium hydroxide, 150 ml.

of water and 75 ml. of epichlorohydrin was stirred under nitrogen at room temperature for 1.5 hours. The aqueous layer was separated, made slightly acidic with acetic acid and extracted with chloroform. The chloroform extracts were washed successively with water and saturated aqueous sodium chloride, dried over anhydrous sodium sulfate, and evaporated to dryness under vacuum to give 11.0 g. of partially crystalline product indicated by nmr spectroscopy to comprise a mixture of 1-chloro-3-[4-hydroxy-3-(methylsulfinyl)phenoxy]-2-propanol and 3-[4-hydroxy-3-(methylsulfinyl)phenoxy]-1,2-epoxypropane. This material was combined with 80 ml. of t-butylamine in 150 ml. of 2-propanol and the resulting mixture was heated overnight under reflux. The reaction mixture was evaporated to dryness under vacuum and the residue was adsorbed on a column of silica gel. Elution with ethyl acetate afforded 6.0 g. of the desired product which was converted to the hydrochloride in conventional manner. Recrystallization from methanol-isopropanolacetonitrile afforded 5.6 g. of the hydrochloride as a white crystalline solid. This material was combined with 2.3 g. of product obtained in another similar preparation and recrystallized from absolute ethanol-ether to give 6.2 g. of 1-(t-butylamino)-3-[4-hydroxy-3-(methylsulfinyl)phenoxy]-2-propanol hydrochloride ethanolate [Formula I: $Y=CH_3SO$, $R_1=H$, $R_2=C(CH_3)_3$], m.p. 140°–145° C.

EXAMPLE 5

A. To a stirred solution containing 21.0 g. of 2-(methylthio)-1,4-hydroquinone in 200 ml. of methanol and 70 ml. of acetic acid was added dropwise over 0.5 hour 44 ml. of 40% peracetic acid. After the addition was complete, stirring was continued an additional two hours. The reaction mixture was then evaporated to dryness and the residue dissolved in ethyl acetate. The ethyl acetate solution was washed successively with saturated aqueous sodium bicarbonate, dilute hydrochloric acid and saturated aqueous sodium chloride, dried over anhydrous sodium sulfate, and evaporated to dryness to give, after drying, 24 g. of 2-(methylsulfonyl)-1,4-hydroquinone.

B. A mixture containing 24 g. of 2-(methylsulfonyl)-1,4-hydroquinone, 10.5 g. of sodium hydroxide, 225 ml. of water, 125 ml. of tetrahydrofuran and 125 ml. of epichlorohydrin was stirred 1.25 hours at room temperature. The reaction mixture was then acidified with acetic acid and extracted thoroughly with ethyl acetate. The organic extracts were washed with water followed by saturated aqueous sodium chloride and then filtered through a 2-inch column of silica gel to remove colored impurities. The filtrate was evaporated and the residue dissolved in 4:1 ether-isopropyl acetate and the resulting solution washed with water and saturated aqueous sodium chloride. The aqueous washes were back extracted with ether and then the organic portions were combined and evaporated to dryness to give 23.8 g. of a yellow gum indicated by nmr spectroscopy to comprise a mixture of 1-chloro-3-[4-hydroxy-3-(methylsulfonyl)phenoxy]-2-propanol and 3-[4-hydroxy-3-(methylsulfonyl)phenoxy]-1,2-epoxypropane. This material was combined with 150 ml. of t-butylamine in 100 ml. of 2-propanol and heated overnight under reflux. The reaction mixture was evaporated to dryness under vacuum, the residue diluted with methylene dichloride and the resulting solution extracted thoroughly with water. The aqueous extracts were evaporated to dryness and the residue adsorbed on a column of silica gel. Elution with 5% methanol in chloroform removed a highly colored impurity. Continued elution with 12% methanol in chloroform afforded 15 g. of desired product which was converted to the methanesulfonate salt in acetonitrile containing a small amount of 2-propanol. The crystalline salt was dissolved in 20 ml. of methanol, diluted to 130 ml. with 2-propanol, concentrated to a volume of 100 ml. and diluted with 40 ml. of ethyl acetate. On standing, the product crystallized to give 9.9 g. of 1-(t-butylamino)-3-[4-hydroxy-3-(methylsulfonyl)phenoxy]-2-propanol methanesulfonate [Formula I: $Y=CH_3SO_2$, $R_1=H$, $R_2=C(CH_3)_3$], m.p. 181°–183° C.

EXAMPLE 6

Following a procedure similar to that described in Example 5B afforded 20 g. of a yellow oil which was combined with 80 ml. of d(+)-1-methyl-3-(4-methoxyphenyl)propylamine and heated 2 hours on a steam bath. Unreacted amine was removed by vacuum distillation (90°–95° C./0.08 mm Hg.). The residue was dissolved in ethyl acetate and the resulting solution washed successively with saturated aqueous sodium bicarbonate and saturated aqueous sodium chloride. The ethyl acetate was evaporated under vacuum and the residue was adsorbed on a 2.5-inch column of silica gel. The product was eluted from the column with 5% methanol in ethyl acetate and converted to the methanesulfonate salt in acetonitrile. The salt was recrystallized from acetonitrile and then partitioned between isopropyl acetate and water. The aqueous layer was evaporated to dryness and the residue was extracted with ethyl acetate. The ethyl acetate extracts were washed with saturated aqueous sodium bicarbonate and evaporated to dryness leaving 16 g. of product which was rechromatographed on silica gel using methylene dichloride as eluent. This material was converted to the acetate salt in conventional manner and crystallized from methanol-acetone to give 9.0 g. of white crystalline solid. Two recrystallizations from methanol-acetone afforded 5.1 g. of 1-[4-hydroxy-3-(methylsulfonyl)phenoxy]-3-[[3-(4-methoxyphenyl)-1-methylpropyl]amino]-2-propanol acetate [Formula I: $Y=CH_3SO_2$, $R_1=H$,

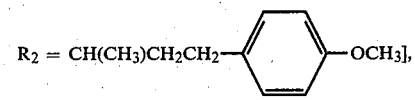

$R_2 = CH(CH_3)CH_2CH_2\text{—}\langle\text{phenyl}\rangle\text{—}OCH_3]$, m.p. 132°–138° C. $[\alpha]_D^{25}=+7.3°$ (2% in methanol). The product obtained in another similar preparation was converted to the corresponding hydrochloride salt, m.p. 143°–145° C. $[\alpha]_D^{25}=+9.95°$ (2% in methanol).

EXAMPLE 7

A. It is contemplated that reacting 4-benzyloxy-3-(methylsulfinyl)phenyl benzoate prepared according to the procedure of Example 3A with cobalt chloride hexahydrate and sodium bobohydride according to the procedure described in Example 1H will give 4-benzyloxy-3-(methylthio)-phenol and that substituting the latter for 4-benzyloxy-3-(methylsulfinyl)phenol in the procedures of Examples 3C and 3D will afford 1-[4-hydroxy-3-(methylthio)phenoxy]-3-[[3-(4-methoxyphenyl)-1-methylpropyl]-amino]-2-propanol (Formula I: $Y=CH_3S$, $R_1=H$,

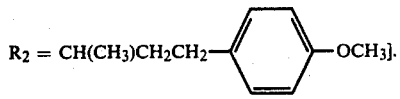

B. It is also contemplated the above product will be obtained by following a procedure similar to that described in Example 1H but substituting the 1-[4-benzyloxy-3-(methylsulfinyl)phenoxy]-3-[[3-(4-methoxyphenyl)-1-methylpropyl]amino]-2-propanol of Example 3C for 1-(t-butylamino)-3-[4-methoxy-3-(methylsulfinyl)phenoxy]-2-propanol, and then debenzylating the resulting 1-[4-benzyloxy-3-(methylthio)-phenoxy]-3-[[3-(4-methoxyphenyl)-1-methylpropyl]amino]-2-propanol [Formula I: Y=CH$_3$S, R$_1$=C$_6$H$_5$CH$_2$,

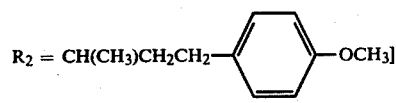

according to the procedure of Example 3D.

EXAMPLE 8

It is contemplated that by following a procedure similar to that described in Example 3C but substituting t-butylamine for d(+)-3-(4-methoxyphenyl)-1-methylpropylamine there will be obtained 1-[4-benzyloxy-3-(methylsulfinyl)phenoxy]-3-(t-butylamino)-2-propanol [Formula I: Y=CH$_3$SO, R$_1$=C$_6$H$_5$CH$_2$, R$_2$=C(CH$_3$)$_3$] and that reduction of this product according to the procedure of Example 1H will produce the corresponding 1-[4-benzyloxy-3-(methylthio)phenoxy]-3-(t-butylamino)-2-propanol [Formula I: Y-CH$_3$S, R$_1$=C$_6$H$_5$CH$_2$, R$_2$=C(CH$_3$)$_3$] which after debenzylation according to the procedure of Example 3D will afford 1-[4-hydroxy-3-(methylthio)-phenoxy]-3-(t-butylamino)-2-propanol [Formula I: Y=CH$_3$S, R$_1$=H, R$_2$=C(CH$_3$)$_3$].

EXAMPLE 9

It is contemplated that by following a procedure similar to that described in Example 4C but substituting isopropylamine, 3-(4-hydroxyphenyl)-1-methylpropylamine, 2-(4-methoxyphenyl)-1-methylethylamine, 4-(4-methoxyphenyl)-1-methylbutylamine or 1-ethyl-2-phenylethylamine for t-butylamine, there will be obtained 1-[4-hydroxy-3-(methylsulfinyl)phenoxy]-3-isopropylamino)-2-propanol, 1-[4-hydroxy-3-(methylsulfinyl)phenoxy]-3-[[3-(4-hydroxyphenyl)-1-methylpropyl]amino]-2-propanol, 1-[4-hydroxy-3-(methylsulfinyl)phenoxy]-3-[[2-(4-methoxyphenyl)-1-methylethyl]amino]-2-propanol, 1-[4-hydroxy-3-(methylsulfinyl)-phenoxy]-3-[[4-(4-methoxyphenyl)-1-methylbutyl]amino]-2-propanol or 1-[(1-ethyl-2-phenylethyl)amino]-3-[4-hydroxy-3-(methylsulfinyl)phenoxy]-2-propanol, respectively [Formula I: Y=CH$_3$SO, R$_1$=H, R$_2$=CH(CH$_3$)$_2$,

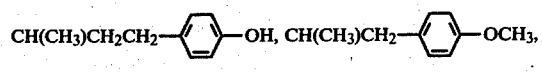

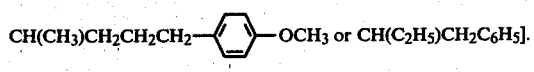

EXAMPLE 10

It is contemplated that by following a procedure similar to that described in Example 5B but substituting propylamine, 1,1-dimethyl-2-phenylethylamine, 2-(3-methylphenyl)ethylamine or 2-(4-isobutoxyphenyl)ethylamine for t-butylamine, there will be obtained 1-[4-hydroxy-3-(methylsulfonyl)phenoxy]-3-(propylamino)-2-propanol, 1-[4-hydroxy-3-(methylsulfonyl)phenoxy]-3-[(1,1-dimethyl-2-phenylethyl)amino]-2-propanol, 1-[4-hydroxy-3-(methylsuflonyl)phenoxy]-3-[[2-(3-methylpehnyl)ethyl]amino]-2-propanol or 1-[4-hydroxy-3-(methylsulfonyl)phenoxy]-3-[[2-(4-isobutoxyphenyl)ethyl]amino]-2-propanol, respectively [Formula I: Y=CH$_3$SO$_2$, R$_1$=H, R$_2$=C$_3$H$_7$, C(CH$_3$)$_2$CH$_2$C$_6$H$_5$,

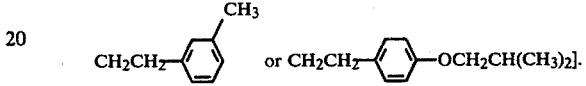

EXAMPLE 11

It is contemplated that by following procedures similar to those described in Examples 5A and 5B but substituting 2-(ethylthio)-1,4-hydroquinone or 2-(butylthio)-1,4-hydroquinone [prepared according to the method of Ukai and Hirose, Chem. Pharm. Bull. 16, 195–201 (1968)] for 2-(methylthio)-1,4-hydroquinone, there will be obtained 1-(t-butylamino)-3-[4-hydroxy-3-(ethylsulfonyl)phenoxy]-2-propanol or 1-(t-butylamino)-3-[4-hydroxy-3-(butylsulfonyl)phenoxy]-2-propanol, respectively [Formula I: Y=C$_2$H$_5$SO$_2$ or C$_4$H$_9$SO$_2$, R$_1$=H, R$_2$=C(CH$_3$)$_3$].

EXAMPLE 12

It is contemplated that by following procedures similar to those described in Examples 1E–1G but substituting butyl iodide for methyl iodide, there will be obtained 1-[4-butoxy-3-(methylsulfinyl)phenoxy]-3-(t-butylamino)-2-propanol [Formula I: Y=CH$_3$SO, R$_1$=C$_4$H$_9$, R$_2$=C(CH$_3$)$_3$] and that reduction of this product according to the procedure of Example 1H will afford 1-[4-butoxy-3-(methylthio)phenoxy]-3-(t-butylamino)-2-propanol [Formula I: Y=CH$_3$S, R$_1$=C$_4$H$_9$, R$_2$=C(CH$_3$)$_3$].

The compounds of this invention having Formula I hereinabove have been shown to have useful antihypertensive and β-adrenergic blocking activity as can be seen by the results of standard pharmacological tests carried out on representative examples as described below.

Antihypertensive activity was determined on the basis of the observed reduction in systolic blood pressure measured according to the method of H, Kersten et al., J. Lab. and Clin. Med., 32, 1090 (1947) following a single oral medication in the unanesthetized spontaneously hypertensive rat described by Okamato et al., Japan Circulation J. 27, 282 (1963).

Beta-adrenergic blocking activity was determined in the pentobarbitalized dog as judged by the ability of the test compound to inhibit the elevation in heart rate elicited by a 0.5 mcg/kg i.v. injection if isoproterenol.

The results of the above-described pharmacological tests are presented in the following table:

| Cpd. of Ex. No. | Antihypertensive Activity SH Rat AHD$_{40}$[a] (mg/kg) p.o. | β-Adrenergic Blocking Activity Anesthetized Dog AED$_{50}$[b] (mg/kg) i.v. |
|---|---|---|
| 1H | >150 (−10)[c] | >0.25 (40%)[d] |
| 1G | >150 (−18) | Ca. 0.10 |
| 2 | >150 (−30) | 0.10 |
| 3D | 50 | 0.015 |
| 4C | 40 | 0.011 |
| 5B | >50 (−10) | 0.25 |
| 6 | 30 | 0.13 |

[a]AHD$_{40}$ = single oral dose required to induce a 40 mm. average reduction in systolic blood pressure in the anesthetized spontaneous hypertensive rat.
[b]AED$_{50}$ = approximate intravenous dose required to cause 50% inhibition of the heart rate increase elicited by isoproterenol in the pentobarbitalized dog.
[c]Actual reduction in systolic blood pressure (mm. Hg) observed at the indicated dose of test compound.
[d]Actual percentage inhibition of isoproterenol-induced heart rate increase above pre-challenge heart rate observed at the indicated dose of test compound.

I claim:
1. A compound having the formula

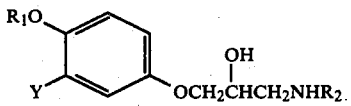

wherein:
Y is lower-alkylthio, lower-alkylsulfinyl or lower-alkylsulfonyl;
R$_1$ is hydrogen, lower-alkyl or benzyl;
R$_2$ is lower-alkyl or

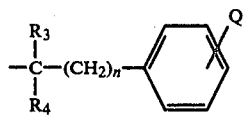

R$_3$ and R$_4$ are independently hydrogen or lower-alkyl;
Q is hydrogen, lower-alkyl, hydroxy or lower-alkoxy; and
n is 1, 2 or 3;
or an acid-addition salt thereof.
2. A compound according to claim 1 where R$_2$ is

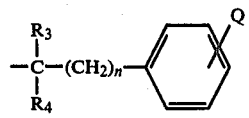

3. A compound according to claim 2 wherein Y is methylthio, methylsulfinyl or methylsulfonyl.
4. A compound according to claim 3 wherein n is 2.
5. A compound according to claim 4 wherein Q is lower-alkoxy.
6. A compound according to claim 5 wherein Y is methylsulfinyl.
7. A compound according to claim 6 wherein R$_1$ is hydrogen.
8. 1-[4-Methoxy-3-(methylsulfinyl)phenoxy]-3-[[3-(4-methoxyphenyl)-1-methylpropyl]amino]-2-propanol or an acid addition salt thereof according to claim 6.
9. 1-[4-Hydroxy-3-(methylsulfinyl)phenoxy]-3-[[3-(4-methoxyphenyl)-1-methylpropyl]amino]-2-propanol or an acid-addition salt thereof according to claim 7.
10. A compound according to claim 5 wherein Y is methylsulfonyl.
11. A compound according to claim 10 wherein R$_1$ is hydrogen.
12. 1-[4-Hydroxy-3-(methylsulfonyl)phenoxy]-3-[[3-(4-methoxyphenyl)-1-methylpropyl]amino]-2-propanol or an acid-addition salt thereof according to claim 11.
13. A compound according to claim 1 wherein R$_2$ is lower-alkyl.
14. A compound according to claim 13 wherein Y is methylthio, methylsulfinyl or methylsulfonyl.
15. A compound according to claim 14 wherein Y is methylthio.
16. 1-(t-Butylamino)-3-[4-methoxy-3-(methylthio)phenoxy]-2-propanol or an acid-addition salt thereof according to claim 15.
17. A compound according to claim 14 wherein Y is methylsulfinyl.
18. A compound according to claim 17 wherein R$_1$ is hydrogen.
19. 1-(t-Butylamino)-3-[4-methoxy-3-(methylsulfinyl)phenoxy]-2-propanol or an acid-addition salt thereof according to claim 17.
20. 1-(t-Butylamino)-3-[4-hydroxy-3-(methylsulfinyl)phenoxy]-2-propanol or an acid-addition salt thereof according to claim 18.
21. A compound according to claim 14 wherein Y is methylsulfonyl.
22. A compound according to claim 21 wherein R$_1$ is hydrogen.
23. 1-(t-Butylamino)-3-[4-hydroxy-3-(methylsulfonyl)phenoxy]-2-propanol or an acid-addition salt thereof according to claim 22.
24. A pharmaceutical composition comprising a compound according to claim 1 in admixture with a pharmaceutically acceptable excipient.
25. A pharmaceutical composition comprising a compound according to claim 2 in admixture with a pharmaceutically acceptable excipient.
26. A pharmaceutical composition comprising a compound according to claim 9 in admixture with a pharmaceutically acceptable excipient.
27. A pharmaceutical composition comprising a compound according to claim 13 in admixture with a pharmaceutically acceptable excipient.
28. The method of lowering blood pressure in a mammal in need of such treatment which comprises administering to said mammal a blood pressure-lowering effective amount of a compound according to claim 1.
29. The method of lowering blood pressure in a mammal in need of such treatment which comprises administering to said mammal a blood pressure-lowering effective amount of a compound according to claim 2.
30. The method of lowering blood pressure in a mammal in need of such treatment which comprises administering to said mammal a blood pressure-lowering effective amount of a compound according to claim 9.
31. The method of lowering blood pressure in a mammal in need of such treatment which comprises administering to said mammal a blood pressure-lowering effective amount of a compound according to claim 13.

* * * * *